United States Patent
Lambert, Jr.

(10) Patent No.: US 6,620,785 B2
(45) Date of Patent: Sep. 16, 2003

(54) TREATMENT OF MYCOBACTERIAL DISEASES BY ADMINISTRATION OF BACTERICIDAL/PERMEABILITY-INCREASING PROTEIN PRODUCTS

(75) Inventor: Lewis H. Lambert, Jr., Fremont, CA (US)

(73) Assignee: Xoma Corporation, Berkeley, CA (US)

(*) Notice: Subject to any disclaimer, the term of this patent is extended or adjusted under 35 U.S.C. 154(b) by 0 days.

(21) Appl. No.: 09/782,642

(22) Filed: Feb. 13, 2001

(65) Prior Publication Data

US 2002/0103118 A1 Aug. 1, 2002

Related U.S. Application Data

(63) Continuation of application No. 08/626,646, filed on Apr. 1, 1996, now Pat. No. 6,214,789, which is a continuation of application No. 08/285,803, filed on Aug. 4, 1994, now abandoned, which is a continuation-in-part of application No. 08/031,145, filed on Mar. 12, 1993, now abandoned.

(51) Int. Cl.$^7$ .............................................. A61K 38/17
(52) U.S. Cl. ................. 514/12; 514/291; 514/355; 514/166; 514/210.09
(58) Field of Search ................. 530/324, 300; 514/12, 2; 424/150.1

(56) References Cited

U.S. PATENT DOCUMENTS

| | | | |
|---|---|---|---|
| 5,032,574 A | 7/1991 | Wilde et al. | 514/12 |
| 5,089,274 A | 2/1992 | Marra et al. | 424/534 |
| 5,171,739 A | 12/1992 | Scott | 514/12 |
| 5,198,541 A | 3/1993 | Elsbach et al. | 435/69.1 |
| 5,234,912 A | 8/1993 | Marra et al. | 514/12 |
| 5,308,834 A | 5/1994 | Scott et al. | 514/12 |
| 5,334,584 A | * 8/1994 | Scott et al. | 514/12 |
| 5,348,942 A | 9/1994 | Little, II et al. | 514/12 |
| 5,763,567 A | 6/1998 | Little | 530/300 |

FOREIGN PATENT DOCUMENTS

| | | |
|---|---|---|
| WO | WO 88/06038 | 8/1988 |
| WO | WO 92/03535 | 3/1992 |
| WO | WO 92/09621 | 6/1992 |
| WO | WO 92/14155 | 8/1992 |
| WO | WO 93/05797 | 4/1993 |
| WO | WO 93/06228 | 4/1993 |
| WO | WO 93/23434 | 11/1993 |
| WO | WO 93/23540 | 11/1993 |
| WO | WO 94/17819 | 8/1994 |
| WO | WO 94/18323 | 8/1994 |
| WO | WO 94/20128 | 9/1994 |
| WO | WO 94/20129 | 9/1994 |
| WO | WO 97/42966 | 11/1997 |
| WO | WO 97/44056 | 11/1997 |

OTHER PUBLICATIONS

In't Veld G, Mannion B, Weiss, J, Elsbach, P. Effects of Bacterial/Permeability–Increasing Protein of Polymorphonuclear Leukocytes on Isolated Baterial Cytoplasmic Membrane Vesicles. Infect. Immun. 1988. 56(5):1203–1208.*

Chatterjee D, Hunter SW, McNeil M, Brennan PJ. Lipoarabinomannan. Multiglycosylated form of the mycobacterial mannosylphosphatidylinositols. J Biol Chem. Mar 25, 1992;267(9):6228–33.*

* cited by examiner

*Primary Examiner*—Karen Cochrane Carlson
*Assistant Examiner*—Sheridan Snedden
(74) *Attorney, Agent, or Firm*—Marshall, Gerstein & Borun

(57) ABSTRACT

The present invention relates to methods for treating a subject suffering from infection with Mycobacteria, such as *M. leprae* or *M. tuberculosis* comprising administering to the subject a composition comprising a bactericidal/permeability-inducing (BPI) protein product alone or in combination with administration of an anti-Mycobacterial antibiotic.

6 Claims, 2 Drawing Sheets

TREATMENT OF MYCOBACTERIAL DISEASES BY ADMINISTRATION OF BACTERICIDAL/PERMEABILITY-INCREASING PROTEIN PRODUCTS

This is a continuation of U.S. application Ser. No. 08/626,646, filed Apr. 1, 1996 now U.S. Pat. No. 6,214,789, which is a continuation of U.S. application Ser. No. 08/285,803, filed Aug. 4, 1994, now abandoned, which is a continuation-in-part of U.S. application Ser. No. 08/031,145, filed Mar. 12, 1993, now abandoned.

BACKGROUND OF THE INVENTION

The present invention relates to methods of treating a subject suffering from infection with Mycobacteria by administration of Bactericidal/Permeability-Increasing Protein (BPI) protein products. Mycobacterium is a non-motile, acid-fast, aerobic, genus of bacteria known to cause grave human and animal diseases, such as tuberculosis and leprosy. Infections caused by *M. avium* are the most common form of disseminated bacterial disease in AIDS patients. Orme, et al., *Infect. and Immun.*, 61(1):338–342 (1993).

The administration of conventional antibiotics to treat Mycobacterial infection is known in the art and has achieved varying success depending on the susceptibility of the bacterial strain, the efficacy and toxicity of the antibiotic(s) employed, the duration of treatment, and numerous other factors. Antimicrobials that have been employed alone or in combination to treat Mycobacterial infections, including those caused by *M. tuberculosis* include isoniazid, rifampin, ethambutol, p-aminosalicylic acid, pyrazinamide, streptomycin, capreomycin, cycloserine, ethionamide, kanamycin, amikacin, amithiozone, rifabutin, clofazimine, arithromycin, clarithromycin, ciprofloxacin and ofloxacin. McClatchy, *Antimycobacterial Drugs: Mechanisms of Action, Drug Resistance, Susceptibility Testing, and Assays of Activity in Biological Fluids*, pp. 134–197, In *Antibiotics in Laboratory Medicine*, 3rd ed., V. Lorian, ed. The Williams & Wilkins Co., Baltimore (1991). As many Mycobacterial strains are drug resistant, serious obstacles exist for control and successful treatment of tuberculosis and other Mycobacterial diseases. Id.

A variety of factors have made treatment of individuals afflicted with Mycobacterial diseases problematic. First, Mycobacteria possess a very hydrophobic cell wall that affords protection against the host's immune system. As Mycobacterial infections tend to be chronic, the pathologies of these organisms are generally due to host response. Also, many Mycobacterial strains are drug-resistant. These and other factors make the development of novel, effective methods for treating Mycobacterial diseases highly desirable.

Mycobacteria are readily distinguished from gram-negative and gram-positive bacteria by acid fast staining due to significant differences in cell wall structure. Gram-negative bacteria are characterized by a cell wall composed of a thin layer of peptidoglycan covered by an outer membrane of lipoprotein and lipopolysaccharide (LPS), whereas gram-positive bacteria have a cell wall with a thicker layer of peptidoglycan with attached teichoic acids, but no LPS. The Mycobacterial cell wall is rich in fatty acids, including a major constituent, lipoarabinomannan (LAM), which is widely distributed within the cell wall of Mycobacterium species. LAM has been purified from both *M. leprae* and *M. tuberculosis*. Hunter et al., *J Biol. Chem.*, 261:12345–12351 (1986). LAM is a serologically active mannose containing phosphorylated lipopolysaccharide that may be membrane associated.

The complex physiological effects of LAM appear to be concentration, time, and source-dependent. For example, Chaterjee et al., *Infect. and Immun.*, 60(3):1249–1253 (1992), reported that, in the first 24 hours following exposure, LAM from an avirulent strain of tuberculosis was 100-fold more potent at stimulating TNF secretion in mouse macrophages than LAM from a virulent strain. LAM concentrations of 0.01–10 µg/ml for the avirulent strain and 0.01–100 µg/ml for the virulent strain were tested, and increased LAM concentration was associated with increased TNF production with LAM from both species.

Macrophage-inhibitory effects of LAM have also been described in the art. LAM purified from both *M. leprae* and *M. tuberculosis* has been reported to be a potent in vitro inhibitor of T-cell lymphokine activation of mouse macrophages. Sibley et al., *Infection and Immunity*, 56(5):1232–1236 (1988). Because the principle efferent role of the macrophage in acquired resistance to intracellular pathogens requires activation by T-cell lymphokines, notably gamma-interferon (IFN-γ), macrophages whose activation-response is inhibited are severely compromised in their capacity for both enhanced microbicidal and tumoricidal activities.

In another study, Sibley et al., *Clin. Exp. Immunol.*, 80(1):141–148 (1990), reported that pretreatment of mouse macrophages with 50 to 100 ug/ml LAM blocked macrophage activation by IFN-γ, but pretreatment with 10 µg/ml LAM did not affect macrophage activation. Thus, it is believed that low concentrations of LAM stimulate cytokine production, at least initially. However, higher concentrations of LAM (50–100 µg/ml or more) appear to block rather than promote macrophage function. Thus, the production of either too much or too little cytokine at different stages of Mycobacterial disease may contribute to Mycobacterial pathogenesis. New methods for blocking the above-characterized physiological effects of LAM molecules are a highly desirable goal in the treatment of subjects that are or that have been infected with Mycobacteria. For the same reasons, new methods by which fluids containing LAM can be decontaminated prior to administration into a subject are also desirable. Neutralization of even small amounts of LAM is desirable, because small amounts of LAM may have the physiological effect of stimulating cytokine production.

Of interest to the background of the invention are the disclosures of PCT/US88/00510, (WO 88/06038) published Aug. 25, 1988, indicating that certain poloxypropylene/polyoxyethylene nonionic surface-active block copolymers can be used with or without conventional antibiotics to treat infection with Mycobacterium. This reference cites studies suggesting that the effects of other nonionic surfactants on tuberculosis are most likely due to modification of surface lipids of Mycobacteria, and not to direct bactericidal effects on Mycobacteria. See e.g. Cornforth et al., *Nature*, 168:150–153 (1951).

Bactericidal/permeability-increasing protein (BPI) is a protein isolated from the granules of mammalian polymorphonuclear neutrophils (PMN), which are blood cells essential in the defense against invading microorganisms. Human BPI protein has been isolated from PMN's by acid extraction combined with either ion exchange chromatography Elsbach, *J. Biol. Chem.*, 254:11000 (1979) or *E. coli* affinity chromatography, Weiss, et al., *Blood*, 69:652 (1987), and has potent bactericidal activity against a broad spectrum of gram-negative bacteria. The molecular weight of human BPI is approximately 55,000 Daltons (55 kD). The amino acid sequence of the entire human BPI protein, as well as the DNA encoding the protein, have been elucidated in FIG. 1 of Gray, et al., *J. Biol. Chem.*, 264:9505 (1989), incorporated herein by reference.

BPI has been shown to be a potent bactericidal agent active against a broad range of gram-negative bacterial species. The cytotoxic effect of BPI was originally established to be highly specific to sensitive gram-negative species, with no toxicity being noted for other non-acid fast, gram-positive bacteria or for eukaryotic cells. The precise mechanism by which BPI kills bacteria is as yet unknown, but it is known that BPI must first attach to the surface of susceptible gram-negative bacteria. It is thought that this initial binding of BPI to the bacteria involves electrostatic interactions between the basic BPI protein and negatively charged sites on lipopolysaccharides (LPS). LPS has been referred to as endotoxin because of the potent inflammatory response that it stimulates. LPS induces the release of mediators by host inflammatory cells which may ultimately result in irreversible endotoxic shock. BPI binds to Lipid A, the most toxic and most biologically active component of LPS.

In susceptible bacteria, it is thought that BPI binding disrupts LPS structure, leads to an activation of bacterial enzymes that degrade phospholipids and peptidoglycans, alters the permeability of the cell's outer membrane, and ultimately causes cell death by an as yet unknown mechanism. BPI is also capable of neutralizing the endotoxic properties of LPS to which it binds. Because of its gram-negative bactericidal properties and its ability to neutralize LPS, BPI can be utilized for the treatment of mammals suffering from diseases caused by gram-negative bacteria, such as bacteremia or sepsis.

An approximately 25 kD proteolytic fragment corresponding to the amino-terminal portion of human BPI holoprotein possesses the antibacterial efficacy of the naturally-derived 55 kD human holoprotein. In contrast to the amino-terminal portion the carboxy-terminal region of the isolated human BPI protein displays only slightly detectable anti-bacterial activity. Ooi, et al., *J. Exp. Med.*, 174:649 (1991). A BPI amino-terminal fragment, expressed from a construct encoding approximately the first 199 amino acid residues of the human BPI holoprotein, has been produced by recombinant means as a 23 kD protein referred to as "rBPI$_{23}$". Gazzano-Santoro et al., *Infect. Immun.* 60:4754–4761 (1992).

While BPI protein products are effective for treatment of conditions associated with gram-negative bacterial infection, there continues to exist a need in the art for products and methods for treatment of other bacterial infections such as infection with Mycobacteria.

SUMMARY OF THE INVENTION

The present invention provides methods of treating a subject suffering from infection with Mycobacteria by administration of a composition comprising a BPI protein product. Therapeutic compositions according to the invention may be administered orally, systemically (such as by intravenous, intramuscular or other injection), or as an aerosol. Mycobacterial disease states subject to treatment according to the invention include tuberculosis, which can be caused by infection with *M. tuberculosis*, leprosy, which can be caused by infection with *M. leprae*, and diseases caused by *M. avium* and other Mycobacteria species. According to preferred methods, anti-Mycobacterial antibiotics such as previously identified and/or surfactants may be administered in combination with the BPI protein product to subjects suffering from infection with Mycobacteria.

According to another aspect of the present invention, compositions comprising a BPI protein product are administered to neutralize LAM's physiological effects on a host. For example, methods are provided for neutralizing the effect of low concentrations of LAM capable of stimulating cytokine production in a host. Methods are also provided for neutralizing the inhibitory effect that higher concentrations of Mycobacterial LAM (i.e. 100 $\mu$g/ml or more) have upon the interferon-mediated activation of macrophages. Specifically, a BPI protein product may be administered to an immunosuppressed subject failing to respond to microbes or tumor cells due to LAM-induced insensitivity of macrophages to activation by T-cell lymphokines.

According to a further aspect of the present invention, a BPI protein product is employed in methods for decontaminating a fluid containing LAM prior to administration of the fluid into a subject. Such decontamination methods of the invention involve contacting the fluid with the BPI protein product prior to administration, under conditions such that LAM forms a complex with the BPI protein product which can be removed from the fluid. Fluids subject to decontamination by the methods of this invention include, but are not limited to, blood, plasma, blood serum, bone marrow, isotonic solutions, pharmaceutical agents, and cell culture agents.

A further aspect of this invention relates to the use of a composition comprising a BPI protein product for the manufacture of a medicament for the therapeutic application of treating any of the aforementioned conditions or infections from which a subject might suffer.

Numerous additional aspects and advantages of the invention will become apparent to those skilled in the art upon considering the following detailed description of the invention, which describes presently preferred embodiments thereof.

DETAILED DESCRIPTION OF THE INVENTION

Figure 1:
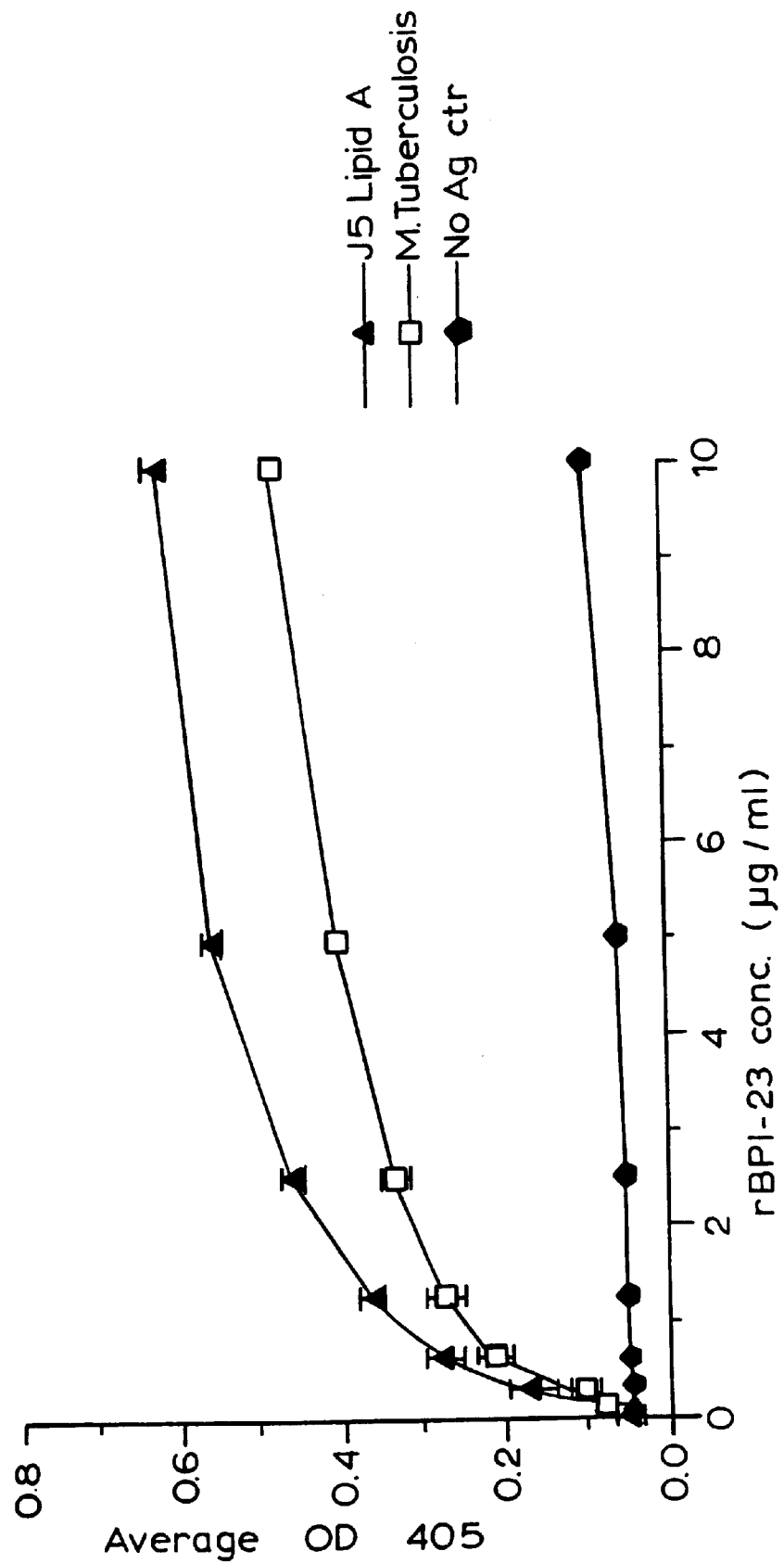
FIG. 1 graphically depicts the results of an assay of BPI protein product binding to *E. coli* J5 Lipid A and *M. tuberculosis* and FIG. 2 graphically represents the results of test to assess the ability of a BPI protein product to inhibit mycobacterial induced TNF production in whole blood.

The present invention relates to the discovery that a composition comprising a BPI protein product can be administered for effective treatment of a subject suffering from infection with Mycobacteria. In particular, the invention provides methods for treatment of leprosy and tuberculosis, grave diseases caused by the species *M. leprae* and *M. tuberculosis*, respectively. It is contemplated that the methods described herein may be used to treat infection with other Mycobacterial species, most notably *M. avium* and *M. intracullulare* (collectively known as "MAC"), but also *M. marinum*, *M. fortuitum*, *M. chelonae*, *M. smegmatis*, *M. kansasii*, *M. bovis*, *M. hominis*, *M. gordonae* and other parthogenic or opportunistic species. Beneficial effects of treatment with BPI protein products are expected to result from binding of the products to LAM and disruption of the bacterial cell wall components (with or without direct killing of the bacteria) in manner similar to that resulting from treatment of gram-negative disease states.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; and biologically active polypeptide analogs of BPI protein or fragments or variants thereof, including cysteine-substituted analogs. The BPI protein products administered according to this invention may be generated and/or isolated by any means known in the art. U.S. Pat. No. 5,198,541, the disclosure of which is hereby incorporated by reference, discloses recombinant genes encoding and methods for expression of BPI proteins including recombinant BPI holoprotein, referred to herein as $rBPI_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 which are hereby incorporated by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same amino acid sequence as a natural human BPI holoprotein, except that the fragment molecule lacks amino-terminal amino acids, internal amino acids, and/or carboxy-terminal amino acids of the holoprotein. Nonlimiting examples of such fragments include an N-terminal fragment of natural human BPI of approximately 25 kD, described in Ooi et al., *J. Exp. Med.*, 174:649 (1991), and the recombinant expression product of DNA encoding N-terminal amino acids from residue 1 to about residue 200, including from about residue 1 to about residue 193 or 199 of natural human BPI, described in Gazzano-Santoro et al., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ. ID NOS:1 and 2) set out in FIG. 1 of Gray et al., supra, with the exceptions noted for $rBPI_{23}$ and with the exception that residue 417 is alanine (specified by GCT) rather than valine (specified by GTI). Other examples include dimeric BPI forms as described in co-owned and co-pending U.S. patent application Ser. No. 08/212,132, filed Mar. 11, 1994, the disclosure of which is hereby incorporated by reference.

Biologically active variants of BPI (BPI variants) include but are not limited to recombinant hybrid fusion proteins, comprising BPI holoprotein or a biologically active fragment thereof and at least a portion of at least one other polypeptide, and dimeric forms of BPI variants. Examples of such hybrid fusion proteins and dimeric forms are described by Theofan et al. in co-owned, copending U.S. patent application Ser. No. 07/885,911, and a continuation-in-part application thereof U.S. patent application Ser. No. 08/064,693 filed May 19, 1993 which are incorporated herein by reference in their entirety and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residue has been replaced by a different amino acid. For example, co-owned, copending U.S. patent application Ser. No. 08/013,801 (Theofan et al., "Stable Bactericidal/Permeability-Increasing Protein Products and Pharmaceutical Compositions Containing the Same," filed Feb. 2, 1993), the disclosure of which is incorporated herein by reference, discloses polypeptide analogs of BPI and BPI fragments wherein a cysteine residue is replaced by a different amino acid. A preferred BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$.

Other BPI protein products useful according to the methods of the invention are peptides derived from or based on BPI produced by recombinant or synthetic means (BPI-derived peptides), such as those described in co-owned and copending U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993), which is a continuation-in-part of U.S. patent application Ser. No. 08/030,644 filed Mar. 12, 1993, the disclosures of which are hereby incorporated by reference. Other useful BPI protein products include peptides based on or derived from BPI which are described in co-owned and co-pending U.S. patent application Ser. No. 08/274,299 filed Jul. 11, 1994, by Horwitz et al. and U.S. patent application Ser. No. 08/273,540, filed Jul. 11, 1994, by Little et al.

Presently preferred BPI protein products include recombinantly-produced N-terminal fragments of BPI, especially those having a molecular weight of approximately between 21 to 25 kD such as $rBPI_{21}$ or $rBPI_{23}$, dimeric forms of these N-terminal fragments. Additionally, preferred BPI protein products include $rBPI_{50}$ and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents. A preferred pharmaceutical composition containing BPI protein products comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another preferred pharmaceutical composition containing BPI protein products comprises the BPI protein product at a concentration of 2 mg/ml in 5 mM citrate, 150 mM NaCl, 0.2% poloxamer 188 and 0.002% polysorbate 80. Such preferred combinations are described in co-owned, co-pending, U.S. patent application Ser. No. 08/190,869 filed Feb. 2, 1994 (McGregor et al., "Improved Pharmaceutical Compositions"), and U.S. patent application Ser. No. 08/012,360 filed Feb. 2, 1993 (McGregor et al., "Improved Pharmaceutical Composition"), the disclosures of which are incorporated herein by reference.

The BPI protein product can be administered by any known method, such as orally, systemically (such as by intravenous, intramuscular or other injection), or as an aerosol. Medicaments can be prepared for oral administration or by injection or other parenteral methods and preferably include conventional pharmaceutically acceptable carriers and adjuvents as would be known to those of skill in the art. The medicaments may be in the form of a unit dose in solid, semi-solid and liquid dosage forms such as tablets, pills, powders, liquid solutions or suspensions, and injectable and infusible solutions. Effective dosage ranges from about 100 µg/kg to about 10 mg/kg of body weight are contemplated. Intravenous administration is a preferred method for treatment of leprosy.

It is contemplated that aerosol administration to the lungs will be a preferred method for treating other Mycobacterial infections, such as tuberculosis. Such aerosol formulations would be manufactured by means that are known in the art, and administered by metered-dose inhaler, updraft nebulization, or other means known in the art.

An aspect of the present invention is to provide methods of treating a subject suffering from any of the physiological effects of Mycobacterial LAM. As described above, the physiological effects of LAM depend on a number of factors, including the source and concentration of the LAM, and the length of time to which host cells are exposed to LAM. Example 3, infra, demonstrates that 20–100 µg/ml of nonviable, desiccated *M. tuberculosis* added to whole blood will stimulate TNF production by the monocytes in the blood. Other studies described above have shown that 50–100 µg/ml of LAM will down-regulate macrophage functions and expression (TNF, and the like) and prevent macrophage activation, said methods comprise administering a BPI protein product to the subject. Methods are provided for treating a subject suffering from the effects of increased cytokine production caused by the physiological presence of LAM. Methods are also provided for treating a subject suffering from LAM-induced inhibition of macrophage activation, and the effects thereof. Methods and formulations by which a BPI protein product may be administered, including preferred methods and formulations, are the same as those set forth above for the treatment of Mycobacterial infection.

Because of the harmful physiological effects that Mycobacterial LAM can have on a subject, even in the absence of viable Mycobacteria, methods are provided in the present invention by which a fluid containing LAM may be decontaminated prior to administration of the fluid into a subject. Such methods comprise contacting the fluid with a BPI protein product prior to administration, under conditions such that LAM forms a complex with the BPI protein product, thereby decontaminating the fluid. By way of nonlimiting examples, such methods may be applied to fluids such as blood, plasma, blood serum, bone marrow, isotonic solutions, pharmaceutical agents, or cell culture reagents.

BPI protein product is thought to interact with a variety of host defense elements present in whole blood or serum, including complement and LBP, and other cells and components of the immune system. Such interactions might result in potentiating and/or synergizing the anti-microbial activities. Because of these interactions, BPI protein products are expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on certain gram-negative bacteria in whole blood or plasma assays than in assays using conventional media. [Weiss et al., *J. Clin. Invest.* 90:1122–1130 (1992)]. This may be because conventional in vitro systems lack the blood elements that facilitate or potentiate BPI's function in vivo, or because conventional media designed to maximize bacterial growth contain higher than physiological concentrations of magnesium and calcium, inhibitors of BPI protein product antibacterial activity.

Therapeutic effectiveness is based on a successful clinical outcome, and does not require that an anti-mycobacterial agent or agents kill 100% of the organism involved in the infection. Frequently, reducing organism load by one log (factor of 10) permits the host's own defenses to control the infection. In addition, augmenting an early anti-mycobacterial effect can be particularly important in addition to any long-term anti-mycobacterial effect. These early events are a significant and critical part of therapeutic success, because they allow time for host defense mechanisms to activate.

It is also contemplated that the BPI protein product be administered with other products that potentiate the anti-mycobacterial activity of BPI protein products. For example, serum complement potentiates the gram-negative bactericidal activity of BPI protein products; the combination of BPI protein product and serum complement provides synergistic bactericidal/growth inhibitory effects. See, e.g., Ooi et al. *J. Biol. Chem.,* 265:15956 (1990) and Levy et al. *J. Biol. Chem.,* 268:6038–6083 (1993) which address naturally-occurring 15 kD proteins potentiating BPI antibacterial activity. See also co-owned, co-pending U.S. patent application Ser. No. 08/093,201 filed Jul. 14, 1993, and continuation-in-part, U.S. patent application Ser. No. 08/274,303 filed Jul. 11, 1994 which describes methods for potentiating gram-negative bactericidal activity of BPI protein products by administering lipopolysaccharide binding protein (LBP) and LBP protein products. The disclosures of these applications are incorporated by reference herein. LBP protein derivatives and derivative hybrids which lack CD-14 immunostimulatory properties are described in co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of which are incorporated by reference herein.

An aspect of this invention includes the use of a composition comprising a BPI protein product for the manufacture of a medicament for the therapeutic application of treating any of the aforementioned conditions or diseases from which a subject suffers. The medicament may include, in addition to a BPI protein product, other chemotherapeutic agents such as known anti-mycobacterial antibiotics or surfactants. The medicament may additionally or alternatively include one or more additional pharmaceutically acceptable components, such as diluents, adjuvants, or carriers.

An aspect of the present invention is the ability to provide more effective treatment of Mycobacterial infection by virtue of the synergistic increase in or potentiation of the anti-bacterial activities of an anti-Mycobacterial antibiotic or BPI protein product. As previously noted, anti-Mycobacterial antibiotic therapy currently involves administration of one or more (and frequently three or more) antibiotics such as isoniazid, rifampin, ethambutol, p-aminosalicylic acid, pyrazinamide, streptomycin, capreomycin, cycloserine, ethionamide, kanamycin, amikacin, amithiozone, rifabutin, clofazimine, arithromycin, clarithromycin, ciprofloxacin and ofloxacin. Unlike some therapeutic agents, BPI protein product is easily administered and produces no inflammatory reaction. An aspect of the present invention is the ability to treat Mycobacterial organisms that are normally resistant to one or more antibiotics. A further aspect is the ability to use lower concentrations of relatively toxic or expensive antibiotics such as rifampin. Because the use of some antibiotics is limited by their systemic toxicity or prohibitive cost, lowering the concentration of antibiotic required for therapeutic effectiveness reduces toxicity and/or cost of treatment, and thus allows wider use of the antibiotic. The present invention may also provide quality of life benefits due to, e.g., decreased duration of therapy, reduced stay in intensive care units or overall in the hospital, with the concomitant reduced risk of serious nosocomial (hospital-acquired) infections.

The invention further provides pharmaceutical compositions for treatment of Mycobacterial infection and the sequelae thereof comprising the combination of a BPI protein product and an antibiotic which is present in an amount effective to have synergistic or potentiating bactericidal/bacteriostatic properties, including increased susceptibility or reversal of resistance. The pharmaceutical composition can comprise a pharmaceutically-acceptable diluent, adjuvant or carrier.

Methods of the present invention are more fully illustrated by the nonlimiting examples which follow. Example 1 address BPI protein products binding to a species of Mycobacterium, M. tuberculosis. Example 2 address prospective use of BPI protein products in binding purified LAM of Mycobacteria. Examples 3 and 4 describe attempts to reverse Mycobacteria-induced cytokine production in whole human blood. Example 5 addresses use of BPI protein products in combination with anti-mycobacterial antibiotics to inhibit M. tuberculosis growth. Remaining Examples 6–13 address prospective in vitro and in vivo use of BPI protein products according to methods of this invention. The models described in those examples and/or other models known in the art are used to predict the efficacy and the optimal BPI protein product formulations of the methods of invention.

EXAMPLE 1

An enzyme linked immunosorbent assay (ELISA) was conducted to determine binding of a BPI protein product to M. tuberculosis. Specifically, non-viable, desiccated M. tuberculosis H37 RA (Difco, Detroit Mich.) was suspended in DPBS (25 µg/ml) and used to coat microtiter wells overnight at 37° C. Wells were also coated with either 25 µg/ml Lipid A (E. coli J5 mutant, RIBI, Hamilton Mont.) or 500 µl DPBS to demonstrate the functionality and specificity of $rBPI_{23}$. After washing (3× with DPBS+0.05% Tween 20), the plates were blocked for 1 hr. at room temperature with 200 µl/well of DPBS+1% non-fat milk. After washing as above, 50 µl solutions of either various concentrations of $rBPI_{23}$ (in DPBS containing 0.05% Tween 20) or DPBS (negative control) were added to the wells, which were then incubated for 1 hr. at 37° C. The wells were again washed as above, and the amount of $rBPI_{23}$ bound to the wells was determined using an anti-$rBPI_{23}$ mouse monoclonal antibody (designated αBPI MAb-2-4) and an enzyme conjugated anti-murine IgG antibody (HRP-Ab, Zymed #61-0120, San Francisco, Calif.). To each well 100 µl of aBPI MAb-2-4 was added (100 ng/ml in DPBS+0.05% Tween 20), and the plates were incubated 1 hr. at 37° C. After washing as above, 100 µl of HRP-Ab was added (1:1000 in DPBS+0.05% Tween 20) to each well and the plates were again incubated 1 hr. at 37° C. After washing the plates as above, 100 µl substrate in 0.1M citrate plus 1:50 ABTS (20 mg/ml stock) and 1:1000 $H_2O_2$ was added to each well. The plates were incubated 10-30 min. at room temperature, and absorbance readings were taken at 405 nm (OD 405).

The results of the experiment are represented graphically in FIG. 1, which depicts the ability of varying concentrations $rBPI_{23}$ to bind to J5 Lipid A (filled triangles); to M. tuberculosis (open squares); and to the no antigen-free control (filled circles). The abscissa of each measurement represents the concentration of $rBPI_{23}$, and the ordinate represents the average OD 405 measurements from four trials. Error bars reflect the variation in OD 405 readings for each data point.

This experiment demonstrated that $rBPI_{23}$ binds specifically to non-viable desiccated M. tuberculosis. The functionality of the $rBPI_{23}$ used in these experiments was confirmed by the results of the Lipid A (positive control) binding assay, and the specificity of the experiments was confirmed by the lack of binding to the negative control samples.

EXAMPLE 2

In this example, an ELISA Assay is conducted to determine binding of a BPI protein product to the lipoarabinomannan portion of Mycobacteria. The binding activity of BPI protein product (e.g., $rBPI_{23}$) to LAM is demonstrated as described in the previous example, except LAM purified from a species of Mycobacterium, (e.g., M. tuberculosis or M. leprae) is substituted for the nonviable M. tuberculosis used to coat the ELISA plates in that example. Purified LAM is isolated as described by Hunter et al., J. Biol. Chem., 261:12345–12351 (1986). Specific binding of biologically active BPI protein product is demonstrated by comparison of the OD 405 readings from the LAM coated wells with positive and negative controls.

EXAMPLE 3

The following experiment was conducted to determine the effect of a BPI protein product, $rBPI_{23}$, on Mycobacteria-induced cytokine production in whole human blood. Whole human blood from healthy volunteers was collected into Vacutainer tubes (ACD, Beckton Dickinson, Rutherford, N.J.), Aliquots of blood (225 µl) were mixed with either $rBPI_{23}$ (10 µg/ml final) or the protein thaumatin (10 µg/ml final in 5 ml) as a negative control. RPMI medium (20 µl) was added to each sample. Varying dilutions (0–8 ng/ml) of either E. coli O113 LPS (Ribi, Hamilton Mont.) or of non-viable, desiccated M. tuberculosis H37 RA (0–100 µg/ml) (Difco, Detroit Mich.) were added to the samples, which were then incubated at 37° C. for 6 hours. The reactions were stopped by the addition of 750 µl of RPMI medium, the samples were centrifuged at 500 g for 7 min, and stored at −20° C. until analyzed. The supernatant was assayed for cytokine (TNF) levels based on a standard curve, according to the manufacturers' recommendation (Biokine ELISA test, T Cell Sciences, Cambridge, Mass.).

The assay results revealed that $rBPI_{23}$ at 10 µg/ml had no inhibitory effect on M. tuberculosis-induced TNF release at the concentration (20–100 µg/ml) of M. tuberculosis added to the blood samples. The same concentration of $rBPI_{23}$ eliminated LPS-induced TNF release at the LPS concentrations tested (2–8 ng/ml). The lack of inhibitory effect on cytokine induction by M. tuberculosis may be the result of use of sub-optimal dosage levels. Alternatively, some component of the Mycobacterial cell wall other than the LAM bound by $rBPI_{23}$ may be responsible for inducing cytokine production at the Mycobacterium concentrations tested.

EXAMPLE 4

In this example, multiple additional assays were conducted to assess the inhibitory effect of BPI protein products on mycobacterial (M. tuberculosis or M. smegmatis) induced production of tumor necrosis factor (TNF) by monocytes/macrophages present in whole human blood. Briefly summarized, live or heat killed mycobacteria at varying concentrations was added to whole blood and incubated with either a fixed amount BPI protein product or acetate buffer negative control solution. After incubation, the content of TNF present was assessed by standard means. The TNF content of BPI protein product treated samples was then compared to the TNF content of buffer control samples to determine the relative inhibitory effect of the BPI protein product tested. Whole blood samples were obtained from healthy human volunteers and aliquoted as in Example 3. To each tube containing 225 μl of whole blood was added from 0 to 1×10$^7$ live or heat killed mycobacteria. Depending on whether one or two BPI protein products were to be tested, four or six tubes were prepared at each concentration of bacteria, after which the tubes were incubated at 37° C. for 15 minutes. To two of the tubes at each bacterial concentration was added either a selected BPI protein product at a final concentration of 4 μg/ml or acetate buffer (as a negative control), after which is tubes were further incubated at 37° C. for 5 to 6 hours. Thereafter 750 μl of RPMI 1640 was added to each sample and the samples were centrifuged at 17,000 rpm (500 g?) for 6 minutes. Supernatants were stored at −70° C. until thawed immediately prior to testing for TNF content using the Biokine ELISA test kit as in Example 3.

In a first series of assays, heat-killed *M. tuberculosis* (strain H37Ra) was employed as the TNF stimulating organism. In a first test on whole blood, no substantial increased in TNF levels was observed until bacteria were added at a concentration of 1×10$^6$ organisms and the presence of rBPI$_{23}$ in the samples resulted in an approximately 70% inhibition of TNF production. In a second test involving two separate whole blood assays, inhibitory effects of both rBPI$_{23}$ and BPI holoprotein were assessed. Substantial increases in TNF concentration over basal levels (no microorganisms added) were observed commencing at microorganism concentrations of 3×10$^5$ up through 1×10$^7$. Overall, inhibition of TNF production by 20% or greater was observed when rBPI$_{23}$ was added at all such organism levels. Lesser degrees of inhibition were noted for the BPI holoprotein (with no inhibition at all noted in one duplicate test at the highest concentration of organisms). The lesser effects of the holoprotein in these assays are likely attributable to the lower molar concentration employed. A third *M. tuberculosis* test was performed on whole blood drawn from four different volunteers, using rBPI$_{23}$ as the test compound. Expectedly, the level of inhibition of TNF formation by the uniform dose of BPI protein product varied from subject to subject. With the exception of one subject's blood samples (wherein inhibition was observed only at intermediate microorganism concentration of 1×10$^6$ and not at all at concentrations of 1×10$^7$), the BPI protein product provided for at least about 10% and up to about 50% TNF inhibition, with higher inhibitory levels being observed at higher microorganism concentrations. A fourth test involving *M. tuberculosis* was carried out using rBPI$_{23}$ at 4 μg/ml and 8 μg/ml concentrations. The BPI protein product was again observed to inhibit TNF at the 4 μg/ml level, with the greatest effects being observed at microorganism concentrations of 3×10$^6$. Doubling the concentration of test compound to 8 μg/ml did not enhance, and in fact somewhat diminished, inhibitory effects observed.

Figure 2:
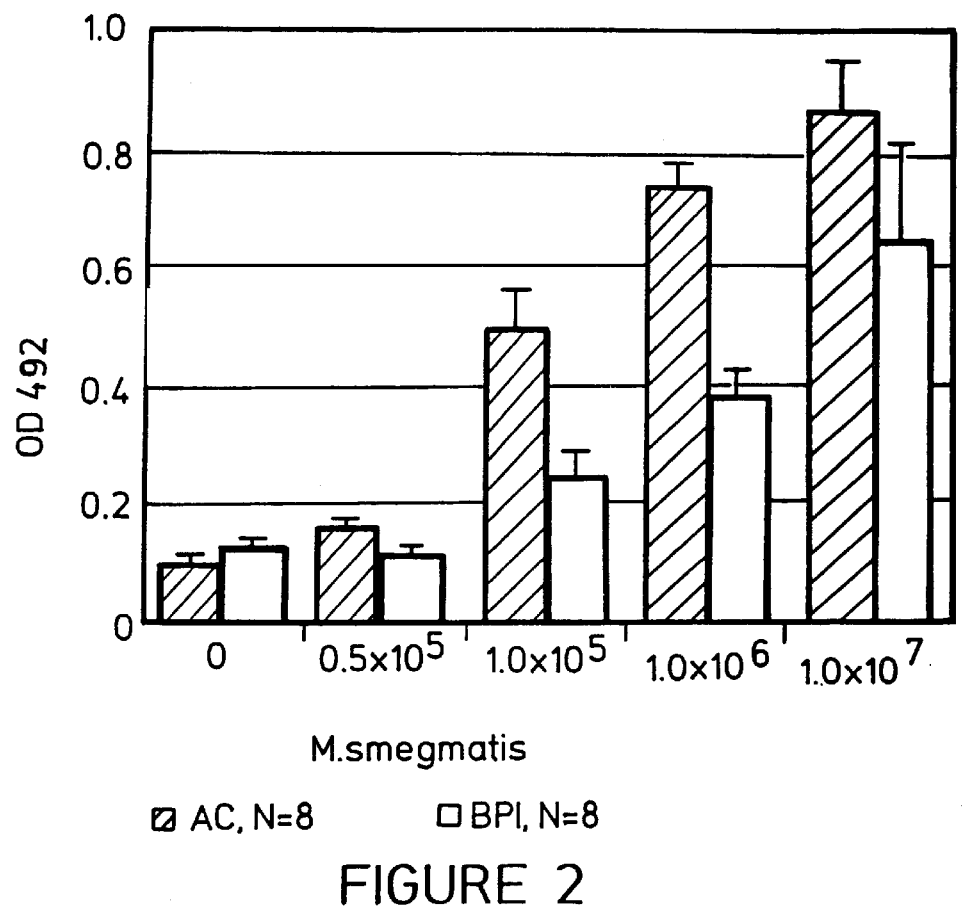

In a second series of assays, heat killed *M. smegmatis* was employed to stimulate TNF production in whole blood. In a first test, whole blood from eight different patients was employed and was subjected to contact with concentrations of 0, 0.5×10$^5$, 1×10$^5$, 1×10$^6$ and 1×10$^7$ organisms. FIG. 2 provides a graphic representation of the sum of the results observed and indicated that the rBPI$_{23}$ product tested at 4 μg/ml was an effective inhibitor of TNF production at all bacterial concentrations. In a second test involving blood from two different subjects, TNF production inhibitory effects of rBPI$_{23}$ were assessed for *M. smegmatis, E. coli* and *S. aureus*. Expectedly, significant TNF inhibitory effects were observed in the *E. coli* treated blood, with the greatest present with microorganism concentrations of 1×10$^5$ and the lesser effects at higher concentrations of organisms. Similarly, no substantial TNF inhibitory effects were observed for the BPI protein product in the *S. aureus* assay. Variable results were seen in the *M. smegmatis* assay; pronounced inhibitory effects were observed in one subject's blood at the 1×10$^7$ concentration of organisms, while inhibition was observed in the other blood sample only at the 1×10$^6$ microorganism concentration.

The above assay results demonstrate in vitro effectiveness of BPI protein products in inhibiting induction of tumor necrosis factor by mycobacterial species and are predictive of in vivo efficacy in human patients.

EXAMPLE 5

In this example, rBPI$_{23}$ at varying concentrations was assessed for its growth inhibitory effect on *M. tuberculosis* treated with varying concentrations of the anti-Mycobacterial antibiotics isoniazid (INH) and rifampin (RMP). Briefly summarized, pure cultures of *M. tuberculosis* (MTB) were incubated for 24 hours with varying concentrations of rBPI$_{23}$ and antibiotic. Cultures were added to Bactec® bottles (Johnston Laboratories, Cockeysville, Md.) containing $^{14}$C labeled nutrients and daily "growth index" values were determined accordingly to the supplier's instructions on the basis of $^{14}$CO$_2$ evolved from the medium. In separate assays, concentrations of rBPI$_{23}$ of 0, 3.9, 15.6, 62.5, 250 and 1000 μg/ml were combined with INH at levels of 0, 0.006, 0.012, 0.025 and 0.05 μg/ml or RMP levels of 0, 0.12, 0.25, 0.5 and 1.0 μg/ml. Growth index values were assessed daily starting the second day after inoculation into the vials through to the eighteenth day. In the INH assay, no BPI protein product was added, growth index values characteristically gradually increased over time and as a function of the dosage of antibiotic employed (increases generally began earlier and rose more steeply at lower doses than at higher doses). Addition of rBPI$_{23}$ had variable effects in enhancing or diminishing antibiotic effects on growth index values, depending on the concentration employed. An intermediate dose (62.5 μg/ml) of BPI protein product consistently tended to reduce growth index values at all doses of INH tested and thus operated to enhance INH growth inhibitory effects. Similar but less pronounced enhancement effects were observed for the 15.6 μg/ml rBPI$_{23}$ dose. Lower (0 and 3.9 μg/ml) and higher (250 and 1000 μg/ml) doses of the BPI protein product generally diminished the antibiotic effects of INH, with the highest rBPI$_{23}$ dose invariably functioning to increasing "swamp out" INH effects on growth index toward the middle of the test period. At later times in the test period, however, the highest doses of BPI protein product appeared to suppress and actually reverse the above-noted characteristic increases in growth index over time. In combinative assay with RMP, rBPI$_{23}$ had no discernible enhancing effect at the highest doses of the antibiotic 0.5 and 1.0 μg/ml where there was essentially no increase in growth index throughout the entire test period. At lesser concentrations of RMP, there tended to be a dose-dependent enhancement effect of the BPI protein product, with the greatest degree of enhancement occurring at the highest doses of $rBPI_{23}$ and no evidence of the "swamp out" effects observed for combinations with INH intermediate times within the test period.

The results set out above establish utility of BPI protein product concurrently filed in enhancing the growth inhibitory effects of anti-mycobacterial antitiotics.

EXAMPLE 6

The following experiment is conducted to determine the in vitro inhibitory effect of a BPI protein product on the growth of a Mycobacterium species, *Mycobacterium tuberculosis* (MTB). The procedure can be performed with other cultivable Mycobacterial species and employs concentrations of a BPI protein product that would be readily generated in human serum by ordinary modes of oral or parenteral administration and/or readily delivered to lung surface by aerosol administration. The effects of the BPI protein product can be evaluated with and without non-ionic surfactants, and/or standard antibiotics.

Log phase cultures of antibiotic-sensitive and antibiotic-resistant MTB are incubated in either 7H11 broth medium or whole human blood, to which the following is added: (a) nothing; (b) surfactant; (c) standard MTB antibiotic; (d) antibiotic plus surfactant. Cultures are incubated with varying concentrations of, e.g., $rBPI_{23}$. Duplicate cultures grown in each medium are also left untreated by $rBPI_{23}$ as a negative control. The organisms are placed in Bactec® bottles (Johnston Laboratories, Cockeysville, Md.) containing $^{14}C$ labeled nutrients. $rBPI_{23}$ challenged *M. tuberculosis* growth is determined by measuring the elution of $^{14}CO_2$ from the medium, compared to the appropriate negative control. The absence of the formation $^{14}CO_2$ by the treated cultures is indicative of the inhibitory affects of $rBPI_{23}$ to MTB. Differential amounts of $^{14}CO_2$ formed in the absence or presence of standard MTB antibiotics and/or surfactants is indicative of the synergistic or additive effect that a BPI protein product has when used conjunctively with such agents. By comparing the results of this experiment performed with varying concentrations of the BPI protein product, the effective concentration of the BPI protein product is optimized. Radiometric assays to test the susceptibility of Mycobacterial species to drugs have been described previously. See McClatchy (cited supra) and references therein.

EXAMPLE 7

The following experiment is conducted to determine the in vitro effects of a BPI protein product ($rBPI_{23}$) in an *M. leprae* model. A palmitic acid oxidation assay is used to measure the "viability" of the uncultivable leprosy bacillus adhered to filter paper and "grown" in a $^{14}C$-palmitic acid-containing medium. In this method $^{14}CO_2$ evolved from the metabolism by *M. leprae* of $^{14}C$-palmitic acid is trapped on filter paper moistened with NaOH and radioactivity is determined with a liquid scintillation counter. Susceptibility to BPI protein product formulations is determined by differences in radioactivity for *M. leprae* tested with such formulations and treated control cultures.

EXAMPLE 8

The following experiment, which is a variation of an assay conducted by Mittal et al., *J. Clin. Microbiol.,* 17(4):704–707 (1983), is conducted to determine the in vitro inhibitory effect of BPI protein product on the growth of *Mycobacterium leprae.* The effects of different concentrations of BPI protein product on *M. leprae* are evaluated with and without non-ionic surfactants, and/or standard antibiotics. The procedures as described by Mittal et al. are outlined below.

Skin biopsy specimens from lepromatous patients are homogenized and are used to inoculate suspensions of mouse peritoneal macrophages cultured in RPMI 1640 (GIBCO Biocult, Irvine, Scotland) enriched with 30% fetal calf serum. After incubating 18 hours, fresh media containing [methyl-$^{3}H$]-thymidine (Amersham International Ltd., Arlington Heights, Ill.) is added and the cultures are incubated for 14 days. The procedure of Mittal et al. is varied by testing the effect of different concentrations of BPI protein product with or without surfactants and/or antibiotics on $^{3}H$-thymidine incorporation. Macrophages containing phagocytosed viable *M. leprae* will incorporate $^{3}H$-thymidine at a 2 to 10-fold higher rate than control cultures containing heat killed *M. leprae*. Greater than 50% inhibition of $^{3}H$-thymidine-incorporation is indicative of bactericidal efficacy of the test product.

EXAMPLE 9

An experiment is conducted to determine the in vivo effect that a BPI protein product will have on *M. tuberculosis* species. The model employed is a variation of that used by Lalande et al., *Antimicrobial Agents and Chemotherapy,* 37(3):407–413 (1993), to assess the efficacy of antimicrobial agents against *M. tuberculosis.* Mice inoculated intravenously with *M. tuberculosis* are treated with various BPI protein product doses alone or in combination with surfactants and/or antibiotics. The efficacy of such treatment regiments is analyzed as described.

EXAMPLE 10

The following experiment is conducted to determine the effect that a BPI protein product will have on *M. leprae* in vivo. The model to be used is a variation of that developed by Shepard to study the effect of compounds on the growth of *M. leprae* in the footpads of infected mice. Shepard et al., *Proc. Soc. Exp. Biol. Med.,* 109:636–638 (1962); Shepard, *J. Exp. Med.* 112:445–454 (1960). Briefly, leprosy bacilli are inoculated into foot-pads of mice, which are subsequently treated with different amounts of test compound with or without known antibiotics and/or surfactants. Untreated infected mice are used as a control. Mice from each treatment regimen are sacrificed at monthly intervals, and sections cut from the infected foot. The presence of an area containing acid-fast bacteria can be observed microscopically and/or the number of such bacteria can be counted. See Shepard and McRae, *Int. J. Lepr.,* 36:78–82. Differences between *M. leprae* bacteria levels observed in treated versus control mice is indicative of the bacteriostatic or bactericidal efficacy of a given BPI treatment regimen. The metabolic status of isolated *M. leprae* may also be measured. Franzblau and Hastings, *Antimicrobial Agnes and Chemotherapy,* 31(5):780–783 (1987).

EXAMPLE 11

The following experiments are designed to demonstrate that BPI protein product is able to inhibit the ability of low concentration of LAM to induce cytokines, yet reverse the unresponsive state that attends higher concentrations of LAM. Increasing concentrations of LAM are pretreated with BPI protein product at varying concentrations. These complexes are applied to peritoneal macrophages from normal and Mycobacterium species infected mice. TNF production by treated cells will be assessed.

EXAMPLE 12

A variation of the armadillo model developed by Kirchheimer et al., *Int. J. Lepr.,* 39:693–702 (1971); Id., 40:229 (1972), is employed to study the in vivo effect of BPI protein product test compositions on the growth of *M. leprae* in infected armadillos. Briefly, leprosy bacilli are inoculated into armadillos, which are subsequently treated with different amounts of a test composition. The test compositions will comprise a BPI protein product, e.g. $rBPI_{23}$, with or without known antibiotics and/or surfactants. Untreated infected specimens are used as a control. Armadillos from each treatment regimen are examined and biopsy specimens analyzed by procedures known in the art. *M. leprae* isolated from armadillos is assayed for metabolic activity. Differences between the appearance of lesions, differences in *M. leprae* bacterial concentrations, and differences in the metabolic activity of *M. leprae* isolates in treated versus control specimens are indicative of the bacteriostatic or bactericidal efficacy of a given BPI treatment regimen.

EXAMPLE 13

The following experiment is conducted to determine the level of decontamination of a fluid containing LAM that can be achieved by treatment with a BPI protein product. Whole human blood, plasma, blood serum or the like is passed through a column containing a matrix, to which a BPI protein product is bound. Such matrix may be constructed by any means known to those skilled in the art. LAM in the fluid complexes with the BPI protein product affixed to the matrix as the fluid is passed through the column. The absence of LAM in the fluid eluted from the column demonstrates the effectiveness of a BPI protein product at decontaminating a fluid containing LAM.

Alternatively, monoclonal antibodies with binding specificity for a BPI protein product, such as the antibodies employed in Example 1, are affixed to the matrix. A sufficient amount of a BPI protein product is added to the mixture to bind any LAM present in the fluid. The fluid is purified by passing it through the column. The αBPI antibodies affixed to the column bind the LAM/BPI protein product complex in the fluid, and the fluid eluted from the column is analyzed for the presence or absence of LAM contamination.

Numerous modifications and variations in the practice of the invention are expected to occur to those skilled in the art upon consideration of the foregoing description of the presently preferred embodiments thereof. For example, while the above illustrative examples principally address studies predictive of antibacterial effects in the context *M. tuberculosis* and *M. leprae*, model studies of infection with, e.g., *M. avium* [see, e.g., Brown et al., *Antimicrob. Agents and Therapy,* 37(3):398–402(1993)] are also expected to reveal effectiveness of BPI protein product therapies. As another example, preliminary experimental data indicates that BPI protein products alone and/or in combination with cytokines such as gamma interferon (and in combination with antibiotics as well) can enhance the rate at which human monocytes phagocytize Mycobacterial organisms. Combinative therapies involving administration of cytokines along with BPI protein products (and antibiotics) are thus within the scope of the invention). Consequently, the only limitations which should be placed upon the scope of the present invention are those which appear in the appended claims.

I claim:

1. A method for decontaminating a fluid containing lipoarabinomannan, said method comprising contacting the fluid with a BPI protein product under conditions such that lipoarabinomannan therein binds the BPI protein product and separating said BPI protein product bound to lipoarabinomannan from said fluid.

2. The method of claim 1, wherein the fluid is selected from the group consisting of blood, plasma, blood serum, and a fluid comprising bone marrow.

3. The method of claim 1, wherein the fluid is selected from the group consisting of an isotonic solution, a fluid comprising a pharmaceutical agent, and a fluid comprising a cell culture reagent.

4. A method of neutralizing lipoarabinomannan in a fluid containing lipoarabinomannan, said method comprising contacting the fluid with a BPI protein product under conditions such that the BPI protein product binds and neutralizes said lipoarabinomannan.

5. The method of claim 4 wherein the fluid is selected from the group consisting of blood, plasma, blood serum, and a fluid comprising bone marrow.

6. The method of claim 4 wherein the fluid is selected from the group consisting of an isotonic solution, a fluid comprising a pharmaceutical agent, and a fluid comprising a cell culture reagent.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1813 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 31..1491

(ix) FEATURE:
      (A) NAME/KEY: mat_peptide
      (B) LOCATION: 124..1491

(xi) SEQUENCE DESCRIPTION: SEQ ID NO: 1:

```
CAGGCCTTGA GGTTTTGGCA GCTCTGGAGG ATG AGA GAG AAC ATG GCC AGG GGC      54
                                Met Arg Glu Asn Met Ala Arg Gly
                                -31 -30                     -25

CCT TGC AAC GCG CCG AGA TGG GTG TCC CTG ATG GTG CTC GTC GCC ATA      102
Pro Cys Asn Ala Pro Arg Trp Val Ser Leu Met Val Leu Val Ala Ile
        -20                 -15                 -10
```

-continued

```
GGC ACC GCC GTG ACA GCG GCC GTC AAC CCT GGC GTC GTG GTC AGG ATC         150
Gly Thr Ala Val Thr Ala Ala Val Asn Pro Gly Val Val Val Arg Ile
            -5                      1                   5

TCC CAG AAG GGC CTG GAC TAC GCC AGC CAG CAG GGG ACG GCC GCT CTG         198
Ser Gln Lys Gly Leu Asp Tyr Ala Ser Gln Gln Gly Thr Ala Ala Leu
 10                  15                  20                  25

CAG AAG GAG CTG AAG AGG ATC AAG ATT CCT GAC TAC TCA GAC AGC TTT         246
Gln Lys Glu Leu Lys Arg Ile Lys Ile Pro Asp Tyr Ser Asp Ser Phe
                 30                  35                  40

AAG ATC AAG CAT CTT GGG AAG GGG CAT TAT AGC TTC TAC AGC ATG GAC         294
Lys Ile Lys His Leu Gly Lys Gly His Tyr Ser Phe Tyr Ser Met Asp
             45                  50                  55

ATC CGT GAA TTC CAG CTT CCC AGT TCC CAG ATA AGC ATG GTC CCC AAT         342
Ile Arg Glu Phe Gln Leu Pro Ser Ser Gln Ile Ser Met Val Pro Asn
         60                  65                  70

GTG GGC CTT AAG TTC TCC ATC AGC AAC GCC AAT ATC AAG ATC AGC GGG         390
Val Gly Leu Lys Phe Ser Ile Ser Asn Ala Asn Ile Lys Ile Ser Gly
     75                  80                  85

AAA TGG AAG GCA CAA AAG AGA TTC TTA AAA ATG AGC GGC AAT TTT GAC         438
Lys Trp Lys Ala Gln Lys Arg Phe Leu Lys Met Ser Gly Asn Phe Asp
 90                  95                 100                 105

CTG AGC ATA GAA GGC ATG TCC ATT TCG GCT GAT CTG AAG CTG GGC AGT         486
Leu Ser Ile Glu Gly Met Ser Ile Ser Ala Asp Leu Lys Leu Gly Ser
                110                 115                 120

AAC CCC ACG TCA GGC AAG CCC ACC ATC ACC TGC TCC AGC TGC AGC AGC         534
Asn Pro Thr Ser Gly Lys Pro Thr Ile Thr Cys Ser Ser Cys Ser Ser
                125                 130                 135

CAC ATC AAC AGT GTC CAC GTG CAC ATC TCA AAG AGC AAA GTC GGG TGG         582
His Ile Asn Ser Val His Val His Ile Ser Lys Ser Lys Val Gly Trp
            140                 145                 150

CTG ATC CAA CTC TTC CAC AAA AAA ATT GAG TCT GCG CTT CGA AAC AAG         630
Leu Ile Gln Leu Phe His Lys Lys Ile Glu Ser Ala Leu Arg Asn Lys
155                 160                 165

ATG AAC AGC CAG GTC TGC GAG AAA GTG ACC AAT TCT GTA TCC TCC AAG         678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT         726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT         774
Val Ala Gly Ile Asn Tyr Gly Leu Val Ala Pro Pro Ala Thr Thr Ala
                205                 210                 215

GAG ACC CTG GAT GTA CAG ATG AAG GGG GAG TTT TAC AGT GAG AAC CAC         822
Glu Thr Leu Asp Val Gln Met Lys Gly Glu Phe Tyr Ser Glu Asn His
            220                 225                 230

CAC AAT CCA CCT CCC TTT GCT CCA CCA GTG ATG GAG TTT CCC GCT GCC         870
His Asn Pro Pro Pro Phe Ala Pro Pro Val Met Glu Phe Pro Ala Ala
            235                 240                 245

CAT GAC CGC ATG GTA TAC CTG GGC CTC TCA GAC TAC TTC TTC AAC ACA         918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA         966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC        1014
Asp Asp Met Ile Pro Lys Glu Ser Lys Phe Arg Leu Thr Thr Lys Phe
                285                 290                 295

TTT GGA ACC TTC CTA CCT GAG GTG GCC AAG AAG TTT CCC AAC ATG AAG        1062
Phe Gly Thr Phe Leu Pro Glu Val Ala Lys Lys Phe Pro Asn Met Lys
```

-continued

```
          300                 305                    310
ATA CAG ATC CAT GTC TCA GCC TCC ACC CCG CCA CAC CTG TCT GTG CAG    1110
Ile Gln Ile His Val Ser Ala Ser Thr Pro Pro His Leu Ser Val Gln
    315                 320                 325

CCC ACC GGC CTT ACC TTC TAC CCT GCC GTG GAT GTC CAG GCC TTT GCC    1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC    1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA    1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT    1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA    1350
Gly Pro Phe Pro Val Glu Leu Leu Gln Asp Ile Met Asn Tyr Ile Val
    395                 400                 405

CCC ATT CTT GTG CTG CCC AGG GTT AAC GAG AAA CTA CAG AAA GGC TTC    1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG    1446
Pro Leu Pro Thr Pro Ala Arg Val Gln Leu Tyr Asn Val Val Leu Gln
                430                 435                 440

CCT CAC CAG AAC TTC CTG CTG TTC GGT GCA GAC GTT GTC TAT AAA        1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC   1551

ACCGGCTGCC TTTCCCCAGG GAATCCTCTC CAGATCTTAA CCAAGAGCCC CTTGCAAACT   1611

TCTTCGACTC AGATTCAGAA ATGATCTAAA CACGAGGAAA CATTATTCAT TGGAAAAGTG   1671

CATGGTGTGT ATTTTAGGGA TTATGAGCTT CTTTCAAGGG CTAAGGCTGC AGAGATATTT   1731

CCTCCAGGAA TCGTGTTTCA ATTGTAACCA AGAAATTTCC ATTTGTGCTT CATGAAAAAA   1791

AACTTCTGGT TTTTTTCATG TG                                           1813
```

(2) INFORMATION FOR SEQ ID NO: 2:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Arg Glu Asn Met Ala Arg Gly Pro Cys Asn Ala Pro Arg Trp Val
-31 -30                 -25                 -20

Ser Leu Met Val Leu Val Ala Ile Gly Thr Ala Val Thr Ala Ala Val
-15                 -10                  -5                   1

Asn Pro Gly Val Val Arg Ile Ser Gln Lys Gly Leu Asp Tyr Ala
                5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
50                  55                  60                  65
```

-continued

```
Ser Gln Ile Ser Met Val Pro Asn Val Gly Leu Lys Phe Ser Ile Ser
                70                  75                  80
Asn Ala Asn Ile Lys Ile Ser Gly Lys Trp Lys Ala Gln Lys Arg Phe
            85                  90                  95
Leu Lys Met Ser Gly Asn Phe Asp Leu Ser Ile Glu Gly Met Ser Ile
        100                 105                 110
Ser Ala Asp Leu Lys Leu Gly Ser Asn Pro Thr Ser Gly Lys Pro Thr
    115                 120                 125
Ile Thr Cys Ser Ser Cys Ser Ser His Ile Asn Ser Val His Val His
130                 135                 140                 145
Ile Ser Lys Ser Lys Val Gly Trp Leu Ile Gln Leu Phe His Lys Lys
                150                 155                 160
Ile Glu Ser Ala Leu Arg Asn Lys Met Asn Ser Gln Val Cys Glu Lys
            165                 170                 175
Val Thr Asn Ser Val Ser Ser Lys Leu Gln Pro Tyr Phe Gln Thr Leu
        180                 185                 190
Pro Val Met Thr Lys Ile Asp Ser Val Ala Gly Ile Asn Tyr Gly Leu
    195                 200                 205
Val Ala Pro Pro Ala Thr Thr Ala Glu Thr Leu Asp Val Gln Met Lys
210                 215                 220                 225
Gly Glu Phe Tyr Ser Glu Asn His His Asn Pro Pro Phe Ala Pro
                230                 235                 240
Pro Val Met Glu Phe Pro Ala Ala His Asp Arg Met Val Tyr Leu Gly
            245                 250                 255
Leu Ser Asp Tyr Phe Phe Asn Thr Ala Gly Leu Val Tyr Gln Glu Ala
        260                 265                 270
Gly Val Leu Lys Met Thr Leu Arg Asp Asp Met Ile Pro Lys Glu Ser
    275                 280                 285
Lys Phe Arg Leu Thr Thr Lys Phe Phe Gly Thr Phe Leu Pro Glu Val
290                 295                 300                 305
Ala Lys Lys Phe Pro Asn Met Lys Ile Gln Ile His Val Ser Ala Ser
                310                 315                 320
Thr Pro Pro His Leu Ser Val Gln Pro Thr Gly Leu Thr Phe Tyr Pro
            325                 330                 335
Ala Val Asp Val Gln Ala Phe Ala Val Leu Pro Asn Ser Ser Leu Ala
        340                 345                 350
Ser Leu Phe Leu Ile Gly Met His Thr Thr Gly Ser Met Glu Val Ser
    355                 360                 365
Ala Glu Ser Asn Arg Leu Val Gly Glu Leu Lys Leu Asp Arg Leu Leu
370                 375                 380                 385
Leu Glu Leu Lys His Ser Asn Ile Gly Pro Phe Pro Val Glu Leu Leu
                390                 395                 400
Gln Asp Ile Met Asn Tyr Ile Val Pro Ile Leu Val Leu Pro Arg Val
            405                 410                 415
Asn Glu Lys Leu Gln Lys Gly Phe Pro Leu Pro Thr Pro Ala Arg Val
        420                 425                 430
Gln Leu Tyr Asn Val Val Leu Gln Pro His Gln Asn Phe Leu Leu Phe
    435                 440                 445
Gly Ala Asp Val Val Tyr Lys
450                 455
```